United States Patent

Wynn et al.

(10) Patent No.: US 7,820,962 B2
(45) Date of Patent: Oct. 26, 2010

(54) DETECTION SYSTEMS AND DOPANTS

(75) Inventors: Paul Grant Wynn, Broxted (GB); Henry Paul McIntyre, Watford (GB)

(73) Assignee: Smiths Detection - Watford Limited, Watford Herts (GB)

( * ) Notice: Subject to any disclaimer, the term of this patent is extended or adjusted under 35 U.S.C. 154(b) by 241 days.

(21) Appl. No.: 11/920,000

(22) PCT Filed: May 12, 2006

(86) PCT No.: PCT/GB2006/001739

§ 371 (c)(1), (2), (4) Date: Nov. 7, 2007

(87) PCT Pub. No.: WO2006/123107

PCT Pub. Date: Nov. 23, 2006

(65) Prior Publication Data

US 2009/0039243 A1    Feb. 12, 2009

(30) Foreign Application Priority Data

May 14, 2005    (GB) .................................. 0509874.4

(51) Int. Cl.
*H01J 49/00*    (2006.01)
(52) U.S. Cl. ..................... 250/282; 250/281; 436/56; 436/106; 436/127; 436/130; 436/171; 436/173; 436/181

(58) Field of Classification Search ................. 250/281, 250/282; 436/56, 106, 127, 130, 171, 173, 436/181

See application file for complete search history.

(56) References Cited

U.S. PATENT DOCUMENTS

2004/0043497 A1* 3/2004 Feuer et al. ................... 436/86

OTHER PUBLICATIONS

Buckley et al., "Mass Spectrometric Determination of a Stable Isotope Tracer for Copper in Biological Materials", Mar. 1982, Anal Chem, vol. 54, No. 3, pp. 504-510.*

* cited by examiner

*Primary Examiner*—Jack I Berman
*Assistant Examiner*—Hanway Chang
(74) *Attorney, Agent, or Firm*—Foley & Lardner LLP

(57) ABSTRACT

An ion mobility spectrometer has a drift chamber (1) with an inlet (2) at one end by which a gas or vapor being analyzed is supplied to the chamber. After ionization, molecules are admitted through a gate 8 and flow along a drift region (9) to a collector plate (11). A drift gas is flowed through the drift region against the flow of ionized molecules and is circulated along a flow path (31, 32, 40) and (30), which includes a chamber (50) including a dopant. The dopant is 2,4-pentanedione, which has been found to enhance the detection of a number of compounds especially toxic industrial chemicals and nitrogen compounds, such as those present in the breath of mammals.

12 Claims, 1 Drawing Sheet

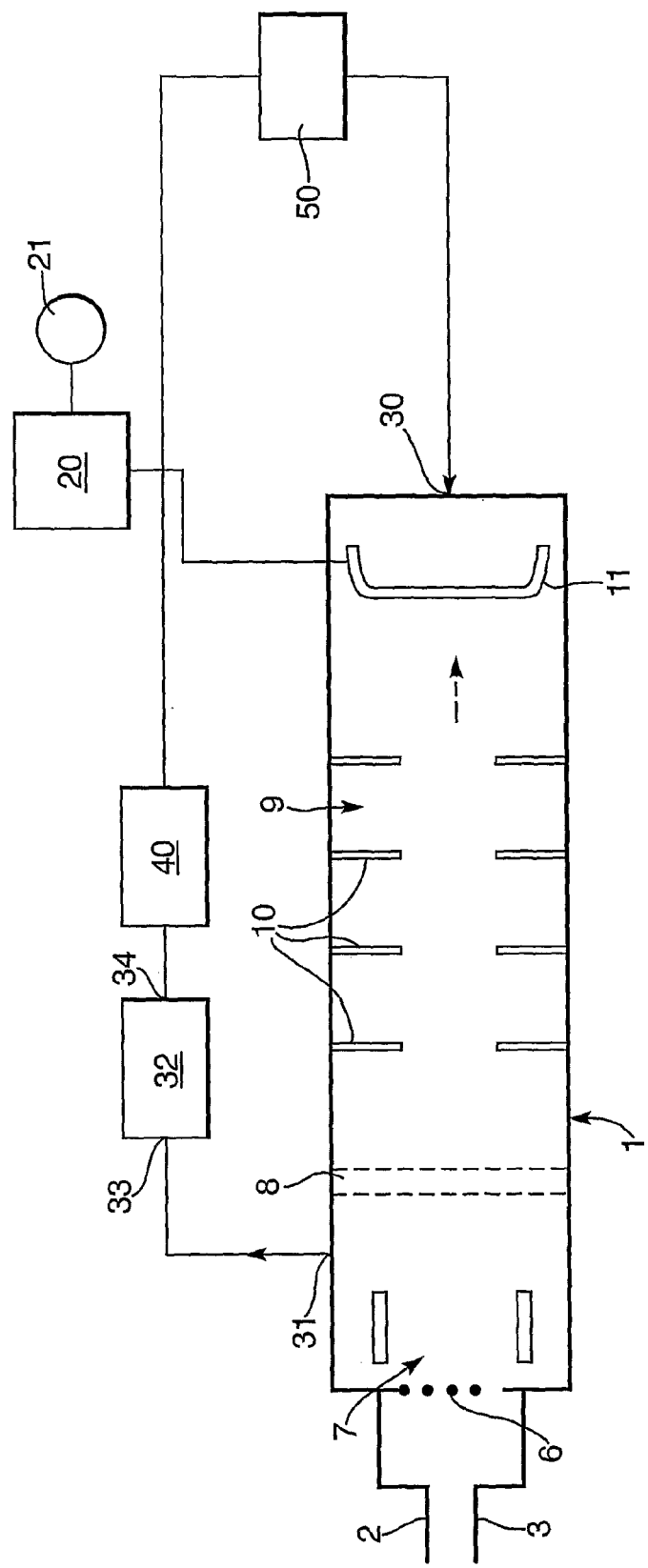

DETECTION SYSTEMS AND DOPANTS

This invention relates to detection systems of the kind by which a vapour or gas can be analysed.

IMS systems are often used to detect substances such as explosives, drugs, blister and nerve agents or the like. An IMS system typically includes a detector cell to which a sample of air containing a suspected substance is supplied as a gas or vapour. The cell operates at or near atmospheric pressure and contains electrodes energized to produce a voltage gradient along the cell. Molecules in the sample of air are ionized, such as by means of a radioactive source, UV source or by corona discharge, and are admitted into the drift region of the cell by an electrostatic gate at one end. The ionized molecules drift to the opposite end of the cell at a speed dependent on the size of the ion. By measuring the time of flight along the cell it is possible to identify the ion. It is common practice to add a reagent or dopant to the cell. The reagent is added to modify the ion-molecule reaction chemistry to achieve at least two aims. One aim is to prevent the ionisation of molecules of low electron or low proton affinity such that they are not detected and hence reduce the opportunity for false alarms. Another aim is to alter the position of one or more ion peaks in the mobility spectrum such that they are shifted from a position close to or neighbouring a peak produced by the compounds to be detected. In this manner the compounds to be detected are more easily identified and quantified. Mass spectrometers may also make use of dopants or reagents.

Examples of IMS systems are described in GB 2324407, GB 2324875, GB2316490, GB2323165, U.S. Pat. No. 4,551,624 and U.S. Pat. No. 6,459,079. U.S. Pat. No. 6,495,824 describes a system where one of several different reagents can be supplied to the cell in response to detection of a suspect substance. U.S. Pat. No. 6,825,460 describes an IMS system having a molecular sieve for drying and cleaning recirculated gases, which is impregnated with a dopant. WO2004/102611 describes an IMS system where several different reagents can be supplied to an IMS cell. The choice of dopant in an IMS or mass spectrometer system can make a significant difference to the ability of the system to discriminate between different substances. Considerable effort has gone into identification of substances that can be effective as dopants.

It is an object of the present invention to provide an alternative detection system and dopant.

According to one aspect of the present invention there is provided a detection system of the above-specified kind, characterised in that the system includes an arrangement for adding as a dopant or reagent a substance including 2,4-pentanedione.

The system may include a detection cell and a flow path for adding gas to the cell, the dopant being added in the flow path. The detection cell may be an IMS drift cell. Alternatively, the detection system may be a mass spectrometer.

According to another aspect of the present invention there is provided an IMS detection system including an IMS drift cell having an inlet for a vapour or gas to be analysed and an arrangement for adding a dopant or reagent to the system to enhance identification of a substance in the vapour or gas, characterised in that the dopant or reagent includes 2,4-pentanedione.

According to a further aspect of the present invention there is provided a method of detecting the presence of a substance including the step of supplying a sample gas or vapour including the substance to detection apparatus, characterised in that the method includes the step of adding a dopant or reagent including 2,4-pentanedione to the sample gas or vapour.

The substance may be a nitrogen compound and, or alternatively a compound present in the breath of mammals According to a fourth aspect of the present invention there is provided a dopant for use in a detection system, the dopant including 2,4-pentanedione.

According to a fifth aspect of the present invention there is provided an IMS dopant including 2,4-pentanedione.

BRIEF DESCRIPTION OF THE DRAWINGS

FIG. 1—shows the IMS system schematically.

The system includes an IMS drift cell 1 having an inlet port 2 by which sample air to be analysed is supplied to the apparatus. The port 2 opens into the left-hand end of the interior of the cell via a selective barrier 6 such as a semi-permeable membrane, or of any other form that allows passage of the molecules of interest whilst excluding the majority of other molecules. Alternatively, the barrier 6 could be non-selective, such as a pinhole, as described in WO93/01485. Instead of a barrier, the sample to be analysed may be supplied to the cell 1 by some other interface, such as of the kind described in EP596978.

The barrier 6 communicates with an ionisation region 7 including an ionisation source such as a radiation source, UV source or a corona discharge. To the right of the ionisation region 7 a Bradbury Nielson gating grid 8 controls passage of ionised molecules into a drift region 9 formed by a series of drift electrodes 10. A collector plate 11 at the right-hand end of the cell 1 collects ions passed through the drift region 9 and provides an output to a processor 20, which also controls the gate 8 and various other functions of the system. The processor 20 provides an output to a display 21 or other utilisation means indicative of the nature of the sample.

At its right-hand end, the cell 1 has an inlet 30, by which recirculated, cleaned, dried drift gas is supplied to the interior of the cell where it travels from right to left and flows out via an exhaust outlet 31 close to the gating grid 8 in the ionisation region 7. Air is supplied to the inlet 30 by means of a pump 32 having an inlet 33 connected to the exhaust outlet 31 and an outlet 34 connected to a molecular sieve 40, which cleans and dries the air exhausted from the drift chamber 9. The air is then passed through a chamber 50 containing the means to administer the dopant vapour in the required concentration range. Typically the dopant will be administered via a permeation source.

As so far described, the system is conventional but the system differs from previous systems in the dopant used in the chamber 50. The dopant used is 2,4-pentanedione, which is also known by the following names: 2,4-pentanedione; acetoacetone; diacetylmethane; pentane-2,4-dione; 2-propanone, acetyl-; 2,4-dioxopentane; 2,4-pentadione; $CH_3COCH_2COCH_3$; acetone, acetyl-; ACAC; pentanedione; pentanedione-2,4; acetyl 2-propanone; UN 2310 or CAS Registry Number: 123-54-6. When used as a dopant, 2,4-pentanedione has been found to be effective both in moving the ion peak of substances of interest away from the position of the Reactant Ion Peak (RIP), and in moving the RIP away from the position of the ion peak of substances of interest. This action enhances and improves the identification and quantification of detected substances which give rise to ion peaks close to the RIP. Typical of these substances are a number of compounds classed as Toxic Industrial Chemicals, such as the acid gases (HCl, HF, etc.), halogens (Cl, F, etc), phosgene, hydrogen cyanide amongst many others. It has been seen to be effective in both positive and negative ion modes of ion mobility spectrometry. It is also believed that this dopant would be effective in detecting nitrogen compounds such as nitrous oxide, nitric oxide and hydrogen peroxide, which are compounds present in the breath of mammals.

It will be appreciated that the dopant need not be added by itself but could be added in combination with other substances, such as other dopants. The dopant need not be added by conventional permeation sources but could be added by adding the dopant to a molecular sieve, such as in the manner described in U.S. Pat. No. 6,825,460.

The invention is not confined to IMS systems but could be used in other detection systems, such as mass spectrometer systems.

The invention claimed is:

1. An IMS dopant comprising 2,4-pentanedione.

2. An IMS detection system comprising (a) an IMS drift cell having an inlet for a vapor or gas to be analyzed and (b) an arrangement for adding a dopant or reagent to the system to enhance identification of a substance in the vapor or gas, wherein the dopant or reagent includes 2,4-pentanedione.

3. A detection system for analyzing a vapor or gas, wherein the system comprises an arrangement for adding as a dopant or reagent a substance including 2,4-pentanedione.

4. A detection system according to claim 3, wherein the system comprises a detection cell and a flow path for adding gas to the cell, and wherein the dopant is added in the flow path.

5. A detection system according to claim 4, wherein the detection cell is an IMS drift cell.

6. A detection system according to claim 3, wherein the detection system is a mass spectrometer.

7. A method of detecting the presence of a substance comprising
   (a) supplying a sample gas or vapor including the substance to detection apparatus; and
   (b) adding 2,4-pentanedione to the sample gas or vapour as a dopant; and
   (c) detecting the presence of the substance.

8. A method according to claim 7, wherein the substance is a nitrogen compound.

9. The method of claim 8, wherein the nitrogen compound is selected from the group consisting of nitrous oxide, nitric oxide, and hydrogen peroxide.

10. A method according to claim 7, wherein the substance includes a compound present in the breath of mammals.

11. The method according to claim 7, wherein the detection apparatus is an IMS device.

12. The method of claim 7, wherein the substance is selected from the group consisting of HCl, HF, halogens, phosgene, and hydrogen cyanide.

* * * * *